United States Patent [19]

Lancranjan

[11] 4,122,190

[45] Oct. 24, 1978

[54] TREATING ACROMEGALY

[75] Inventor: Ioana Lancranjan, Basel, Switzerland

[73] Assignee: Sandoz Ltd., Basel, Switzerland

[21] Appl. No.: 838,631

[22] Filed: Oct. 3, 1977

[30] Foreign Application Priority Data

Oct. 4, 1976 [GB] United Kingdom ............... 41072/76

[51] Int. Cl.² ................. A61K 31/165; A61K 31/415
[52] U.S. Cl. .................................. 424/324; 424/273 R
[58] Field of Search ................................ 424/324, 273

[56] References Cited
PUBLICATIONS

Cryer et al., J. Clin. End. and Met, vol. 39, No. 1, pp. 658-663 (1971).

Primary Examiner—Stanley J. Friedman
Attorney, Agent, or Firm—Gerald D. Sharkin; Robert S. Honor; Thomas O. McGovern

[57] ABSTRACT

α-Adrenoceptor agonists are useful in the treatment of acromegaly.

9 Claims, No Drawings

TREATING ACROMEGALY

IMPROVEMENTS IN OR RELATING TO ORGANIC COMPOUNDS

The present invention relates to a novel use of α-adrenoceptor agonists, e.g. centrally acting alpha receptor stimulating agents such as xylazine, but preferably, methoxamine, and phenylephrine, and especially 2-(2,6-dichlorophenylamino)imidazoline (hereinafter referred to as clonidine) and more especially N-amidino-2-(2,6-dichlorophenyl)acetamide (hereinafter referred to as BS 100-141).

These compounds, suprisingly, inhibit growth hormone secretion in acromegalic subjects, and are therefore useful for the treatment of acromegalic subjects, as indicated in standard tests.

For example, in one test the growth hormone concentration in the blood plasma of acromegalic subjects was determined using standard double anti-body radioimmunoassay techniques on samples collected every half hour over 3 hours after oral administration of from 2 to 3 mg of the compound. A reduction in the growth hormone levels was observed.

For the above-mentioned use the dosage will, of course, vary depending on the compound employed, mode of administration, severity of the disease, and therapy desired. In general, the total daily dosage is in the range from about 0.2 to about 25 mg, and dosage forms suitable for oral administration comprise from about 0.01 mg to about 12 mg of the compounds admixed with a solid or liquid pharmaceutical carrier or diluent, conveniently given in divided doses 2 to 12 times a day or in sustained release form.

Examples of total daily dosages are from 2 to 25 mg, e.g. 8-20 mg, for BS 100-141, and from 0.2 mg to 2 mg, e.g. 0.9 to 1.8 mg, for clonidine.

The compounds may be administered in pharmaceutically acceptable acid addition salt form. Such acid addition salt forms exhibit the same order of activity as the free base forms and are readily prepared in conventional manner. Representative acid addition salt forms include organic acid salt forms such as the hydrogen maleate, fumarate, tartrate and methane sulphonate and mineral acid salt forms such as the hydrochloride, hydrobromide and sulphate. The preferred salt form is, however, the hydrochloride. A pharmaceutical composition may comprise the compound in free base form or in pharmaceutically acceptable acid addition salt form, in association with a pharmaceutical carrier or diluent. Such compositions conveniently contain more than 1% by weight of the compound and may be prepared by conventional techniques to be in conventional forms, for example, capsules, tablets, suppositories, dispersible powders, syrups, elixirs, suspensions or solutions, for enteral or parenteral administration. Preferably BS 100-141 is administered as a solid composition, preferably a solid-filled gelatin capsule or tablet.

Aside from the compound the preparation may contain pharmaceutically inert organic or inorganic adjuvants, optionally granulating agents, lubricants, adhesives, etc. Adjuvants for the production of tablets may be microcrystalline cellulose, mannitol, lactose, etc. Granulating and disintegrating agents may be microcrystalline cellulose, etc. Binding agents may be polyvinylpyrrolidone, methylcellulose and lubricants may be stearic acid, etc. Tablets may be coated or uncoated, with the coating being applied in manner known per se and having the purpose of delaying the disintegration and adsorption in the gastrointestinal tract, and thus providing a retarded effect over a long period. Capsules may contain the active substance either on its own or together with an inert solid diluent, for example, lactose, mannitol, and microcrystalline cellulose.

An example for a tablet formulation is as follows:

| | |
|---|---|
| N-amidino-2-(2,6-dichloro-phenyl)acetamide hydrochloride | 3.45 mg |
| lactose | 88.85 mg |
| microcrystalline cellulose | 12.0 mg |
| polyvinylpyrrolidone | 3.7 mg |
| stearic acid | 2.0 mg |
| | 110.0 mg |

An example of a capsule formulation is as follows:

| | |
|---|---|
| N-amidino-2-(2,6-dichloro-phenyl)acetamide hydrochloride | 3.45 mg |
| lactose | 98.85 mg |
| microcrystalline cellulose | 15.0 mg |
| stearic acid | 2.7 mg |
| | 120.0 mg |

These tablets and capsules (each containing the equivalent of 2 mg BS 100-141 as the free base) are useful in the treatment of acromegaly when administered 3 times a day.

I claim:

1. A method of treating acromegaly in animals which comprises administering an anti-acromegalic effective amount of an α-adrenoceptor agonist selected from the group consisting of N-amidino-2-(2,6-dichlorophenyl)acetamide and clonidine to an animal in need of such treatment.

2. A method of claim 1, wherein the agonist is N-amidino-2-(2,6-dichlorophenyl)acetamide.

3. A method of claim 2, wherein the amount of agonist administered per day is from 0.2 to 25 mg.

4. A method of claim 3, wherein the agonist is administered in unit dosage form containing from 0.01 to 12 mg of the agonist.

5. The method of claim 3 wherein the amount of agonist administered per day is from 2 to 25 mgs.

6. The method of claim 3 wherein the amount of agonist administered per day is from 8 to 20 mgs.

7. The method of claim 1 wherein the agonist is clonidine.

8. The method of claim 7 wherein the amount of agonist administered per day is from 0.2 to 2 mgs.

9. The method of claim 7 wherein the amount of agonist administered per day is from 0.9 to 1.8 mgs.

* * * * *